US00PP25295P3

(12) United States Plant Patent
Klemm et al.

(10) Patent No.: US PP25,295 P3
(45) Date of Patent: Feb. 17, 2015

(54) ***DAHLIA* PLANT NAMED 'KLEDH11031'**

(50) Latin Name: *Dahlia×hybrida*
Varietal Denomination: KLEDH11031

(75) Inventors: Nils Klemm, Stuttgart (DE); Andrea Dohm, Pforzheim (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 226 days.

(21) Appl. No.: 13/573,047

(22) Filed: Aug. 16, 2012

(65) Prior Publication Data

US 2014/0053304 P1 Feb. 20, 2014

(51) Int. Cl.
*A01H 5/00* (2006.01)

(52) U.S. Cl.
USPC ..... Plt./321

(58) Field of Classification Search
CPC ..... A01H 5/025
USPC ..... Plt./321
See application file for complete search history.

*Primary Examiner* — Susan McCormick Ewoldt
*Assistant Examiner* — Louanne Krawczewicz Myer
(74) *Attorney, Agent, or Firm* — Jondle & Associates, P.C.

(57) ABSTRACT

A new and distinct *Dahlia* variety named 'KLEDH11031' particularly distinguished by its large, red-purple flowers, and a full, compact plant habit, is disclosed.

1 Drawing Sheet

Genus and species: *Dahlia×hybrida.*
Variety denomination: 'KLEDH11031'.

BACKGROUND OF THE NEW PLANT

The present invention comprises a new and distinct variety of *Dahlia*, botanically known as *Dahlia×hybrida*, and hereinafter referred to by the variety name 'KLEDH11031'. The new variety is the result of a cross conducted in 2007 in Stuttgart, Germany between female *Dahlia* plant 'DH 2006 0095' (unpatented) and male *Dahlia* plant 'DH 2006 0039' (unpatented). A single plant selection was subsequently chosen for further evaluation and asexual propagation.

The new variety was first asexually propagated by vegetative cuttings in May 2008 in Stuttgart, Germany and has been asexually reproduced repeatedly by terminal tip cuttings for 4 to 5 generations. The present invention has been found to retain its distinctive characteristics through successive asexual propagations.

Plant Breeder's Rights for this variety were applied for in the European Union on Jul. 8, 2011. 'KLEDH11031' has not been made publicly available more than one year prior to filing of this application.

SUMMARY OF THE INVENTION

The following are the most outstanding and distinguishing characteristics of this new variety when grown under normal horticultural practices in Stuttgart, Germany.

1. Large, red-purple flowers; and
2. A full, compact plant habit.

DESCRIPTION OF THE PHOTOGRAPHS

This new *Dahlia* plant is illustrated by the accompanying photograph which shows overall plant habit including blooms, buds, and foliage of the plant. The photograph is of a four month-old plant grown in a heated greenhouse and outside in Stuttgart, Germany in 2012. The colors shown are as true as can be reasonably obtained by conventional photographic procedures.

DESCRIPTION OF THE NEW VARIETY

The following detailed descriptions set forth the distinctive characteristics of 'KLEDH11031'. The data which define these characteristics were collected from asexual reproductions carried out in Stuttgart, Germany. The plant history was taken in May of 2012 on 3 month-old plants grown in 14 centimeter pots. The plants were grown in a heated greenhouse and pinched once at week 7. Color readings were taken under natural light. Color references are primarily to The R.H.S. Colour Chart of The Royal Horticultural Society of London (R.H.S.) (2007 edition).

DESCRIPTION OF THE NEW PLANT

Classification:
- *Family.*—Asteraceae.
- *Botanical name.*—*Dahlia×hybrida.*
- *Common name.*—*Dahlia.*
- *Denomination.*—'KLEDH11031'.

Parentage:
- *Female parent.*—'DH 2006 0095' (unpatented).
- *Male parent.*—'DH 2006 0039' (unpatented).

Growth:
- *Form and habit.*—Inverted triangle.
- *Growth habit.*—Upright.
- *Branching habit.*—Freely branching.
- *Height (from top of soil, including inflorescence).*—25.0 cm to 35.0 cm.
- *Width (including inflorescence).*—Approximately 25.0 cm.
- *Propagation.*—Vegetative cuttings from tips.
- *Time to produce a finished flowering plant.*—Approximately 9 weeks.
- *Time to initiate and develop roots.*—8 to 21 days.

*Root description.*—Fine fibrous.
*Rooting habit.*—Fusiform.

Leaves:
*Leaf quantity per lateral stem.*—6 to 8.
*Type.*—Simple.
*Arrangement.*—Opposite.
*Shape.*—Ovate.
*Apex.*—Acuminate.
*Base.*—Attenuate.
*Margin.*—Serrate.
*Immature leaf.*—Color: Upper surface: RHS N137A. Lower surface: RHS 148C.
*Mature leaf.*—Color: Upper surface: RHS N137A. Lower surface: RHS 139C.
*Length.*—Approximately 11.0 cm.
*Width.*—Approximately 7.0 cm.
*Texture* (*both upper and lower surface*).—Leathery and rough.
*Venation pattern.*—Arcuate.
*Petioles.*—Length: Approximately 3.5 cm. Diameter: Approximately 0.5 cm. Color: RHS 138B. Texture: Smooth.

Stems:
*Total number of branches.*—5.
*Length.*—Approximately 26.0 cm.
*Diameter.*—0.8 cm.
*Internode length.*—Approximately 3.8 cm.
*Color.*—RHS 141C.
*Texture.*—Smooth.

Inflorescence buds:
*Shape.*—Round.
*Length.*—1.2 cm.
*Diameter.*—1.3 cm.
*Color* (*at tight bud just before the ray florets unfold*).—RHS 144B at the apex and RHS 141B at the base.

Inflorescence:
*Type.*—Terminal and composite.
*Height.*—2.0 cm to 3.0 cm.
*Depth.*—2.0 cm to 3.0 cm.
*Blooming habit* (*flowering season*).—Spring to autumn.
*Quantity of inflorescences per plant.*—Approximately 5.
*Lastingness of the inflorescences on the plant.*—20 days.
*Fragrance.*—Absent.
*Inflorescence diameter.*—Approximately 8.5 cm.
*Disc diameter.*—1.6 cm.

Disc floret:
*Quantity per inflorescence.*—30.
*Shape.*—Tubular.
*Tube color* (*closed*).—RHS 7A.
*Tube color* (*mature*).—RHS 6A.
*Length.*—0.8 cm.
*Diameter* (*at apex*).—0.2 cm.
*Apex.*—Five pointed.
*Apex color.*—RHS 7A.
*Base.*—Fused into a corolla tube.
*Margin.*—Entire.

Ray floret:
*Quantity per inflorescence.*—Approximately 20.
*Shape.*—Ovate.
*Color.*—Upper surface: RHS 68B at the apex and RHS 53A at the base. Lower surface: RHS 76B at the apex and RHS 33B at the base.
*Length.*—3.3 cm.
*Width.*—1.8 cm.
*Apex.*—Emarginate.
*Base.*—Fused into a corolla tube.
*Margin.*—Entire.
*Texture* (*both upper and lower surfaces*).—Smooth.
*Peduncle.*—Length: Approximately 5.0 cm. Diameter: 0.3 cm. Texture: Smooth. Color: RHS 143A.

Phyllaries:
*Arrangement.*—Whorled.
*Quantity.*—Approximately 24.
*Shape.*—Lanceolate.
*Color.*—Upper surface: RHS 143B. Lower surface: RHS 143C.
*Length.*—1.6 cm.
*Width.*—0.5 cm.
*Apex.*—Acute.
*Base.*—Obtuse.
*Margin.*—Entire.
*Texture* (*both upper and lower surfaces*).—Smooth shiny.

Reproductive organs:
*Androecium.*—Location: Present on the disc floret. Stamens: Quantity: Approximately 30. Shape: Narrow elliptic. Color: RHS 20A. Filament length: 0.25 cm. Filament diameter: 0.05 cm. Anther: Shape: Narrow elliptic. Color: RHS 20A. Length: 0.3 cm. Diameter: 0.15 cm. Pollen: Color: RHS 16A. Amount: Moderate..
*Gynoecium.*—Location: Present at the base of ray and on the disc florets. Pistils: Number: 30. Length: 1.5 cm. Diameter: 0.3 cm. Stigma: Color: RHS 6A. Shape: Bipartite. Length: 0.3 cm. Diameter: 0.1 cm. Style: Color: RHS 13A. Length: 0.8 cm. Diameter: 0.1 cm. Shape: Filamentous.

Fruit and seed set: Has not been observed.
Disease and insect resistance: Has not been observed.

COMPARISON WITH PARENTAL AND COMMERCIAL VARIETIES

'KLEDH11031' differs from female parent 'DH 2006 0095' (unpatented) in that 'KLEDH11031' has red-purple flowers, whereas 'DH 2006 0095' has apricot-pink red eyed flowers.

'KLEDH11031' differs from male parent 'DH 2006 0039' (unpatented) in that 'KLEDH11031' has red-purple flowers, whereas 'DH 2006 0039' has cream-white yellow eyed flowers.

'KLEDH11031' is similar to the *Dahlia* plants of the HYPNOTICA series in terms of growth habit. 'KLEDH11031' differs from the *Dahlia* plants of the HYPNOTICA series in color pattern. Additionally, 'KLEDH11031' differs from the *Dahlia* plant of the HYPNOTICA series in that 'KLEDH11031' has semi-double flowers and more flowers per plant, whereas *Dahlia* plants of the HYPNOTICA series have double flowers and fewer flowers per plant than 'KLEDH11031'.

We claim:

1. A new and distinct variety of *Dahlia* plant named 'KLEDH11031' as shown and described herein.

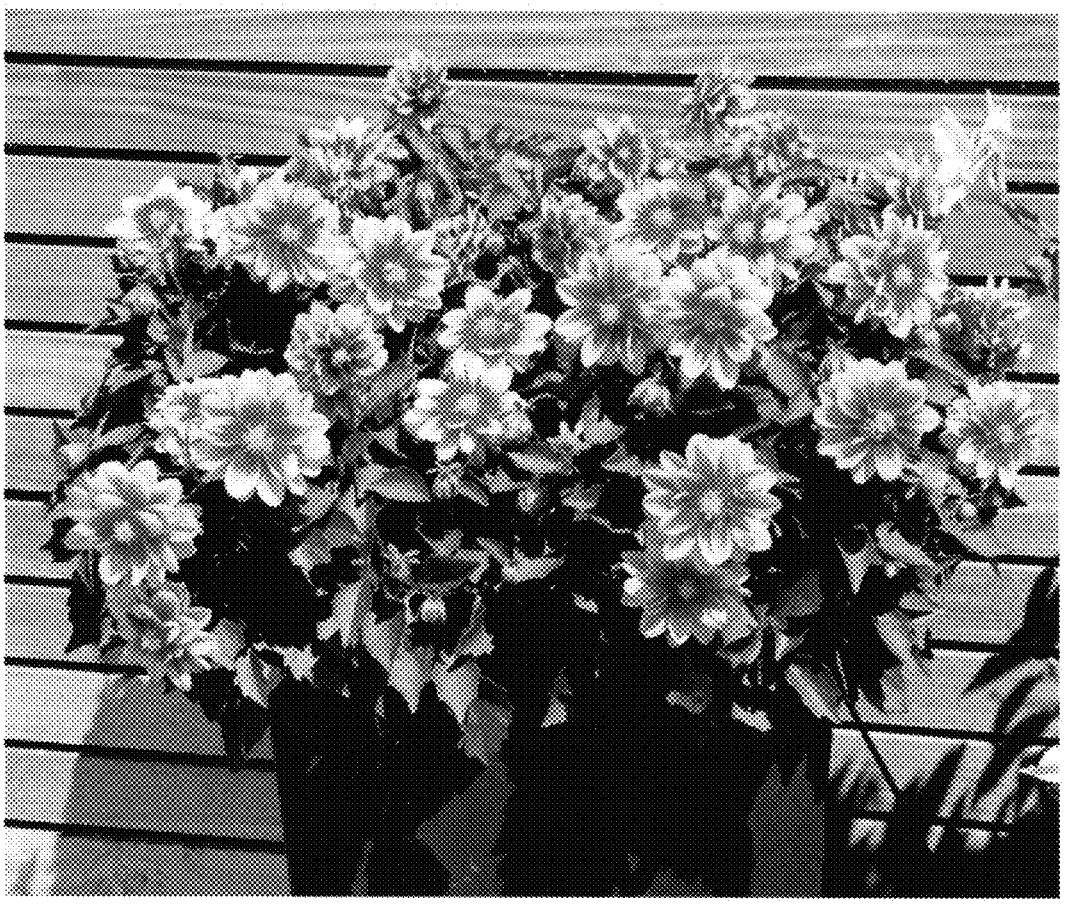

* * * * *